United States Patent
Baumann et al.

(10) Patent No.: US 7,470,962 B2
(45) Date of Patent: Dec. 30, 2008

(54) FIELD EFFECT TRANSISTOR FOR MEASURING BIOCOMPONENTS

(75) Inventors: Werner Baumann, Bühl (DE); Mirko Lehmann, Freiburg (DE); Ingo Freund, Freiburg (DE); Hans-Jurgen Gahle, Emmendingen (DE)

(73) Assignee: Micronas GmbH, Freiburg i. Br. (DE)

( * ) Notice: Subject to any disclaimer, the term of this patent is extended or adjusted under 35 U.S.C. 154(b) by 0 days.

(21) Appl. No.: 10/591,413

(22) PCT Filed: Mar. 1, 2005

(86) PCT No.: PCT/EP2005/002128

§ 371 (c)(1),
(2), (4) Date: Jun. 7, 2007

(87) PCT Pub. No.: WO2005/085829

PCT Pub. Date: Sep. 15, 2005

(65) Prior Publication Data

US 2007/0284630 A1    Dec. 13, 2007

(30) Foreign Application Priority Data

Mar. 2, 2004    (DE) .................. 10 2004 010 635

(51) Int. Cl.
*H01L 31/00* (2006.01)
(52) U.S. Cl. .................. 257/414; 257/414; 257/428; 257/E31.001; 438/48; 438/49
(58) Field of Classification Search .............. 257/414, 257/428, E31.001; 438/48, 49
See application file for complete search history.

(56) References Cited

U.S. PATENT DOCUMENTS

| 5,384,028 | A  | * | 1/1995 | Ito .......................... 257/253 |
| 6,602,399 | B1 |   | 8/2003 | Fromherz et al. |
| 7,053,439 | B2 | * | 5/2006 | Kan et al. ................ 257/315 |
| 7,233,041 | B2 | * | 6/2007 | Duan et al. ............... 257/296 |
| 2002/0050611 | A1 | * | 5/2002 | Yitzchaik et al. ......... 257/315 |

(Continued)

FOREIGN PATENT DOCUMENTS

DE    3835339 A1    4/1989

(Continued)

OTHER PUBLICATIONS

Alfred Stett, et al., "Two-way silicon-neuron interface by electrical induction", Physical Review, 1997, The American Physical Society, vol. 55, No. 2, Feb. 1997.

(Continued)

*Primary Examiner*—Victor A Mandala
(74) *Attorney, Agent, or Firm*—The Webb Law Firm

(57) ABSTRACT

The invention relates to a device for measuring living cells or similar biocomponents comprising a field effect transistor which is provided with a source, a drain and a channel area placed on a substrate. Said channel area connects said source and drain and is provided with a gate-electrode mounted thereon. The gate electrode has at least two laterally disposed parallel electrode areas which are perpendicular to a direction in which the channel area connects the source to the drain in such a way that they are distant and electrically insulated from each other.

11 Claims, 3 Drawing Sheets

U.S. PATENT DOCUMENTS

| | | |
|---|---|---|
| 2005/0045875 A1* | 3/2005 | Lai et al. ............... 257/40 |
| 2005/0184294 A1* | 8/2005 | Zhang ................. 257/77 |
| 2006/0054936 A1* | 3/2006 | Lieber et al. ........... 257/210 |
| 2006/0102935 A1* | 5/2006 | Yitzchaik et al. ....... 257/253 |
| 2007/0023830 A1* | 2/2007 | Pfirsch et al. .......... 257/341 |
| 2007/0063304 A1* | 3/2007 | Matsumoto et al. ..... 257/462 |
| 2007/0072336 A1* | 3/2007 | Yu et al. ............... 438/99 |
| 2007/0170514 A1* | 7/2007 | Mauder et al. ......... 257/370 |
| 2007/0210349 A1* | 9/2007 | Lu et al. ............... 257/252 |

FOREIGN PATENT DOCUMENTS

| | | |
|---|---|---|
| DE | 19623517 C1 | 8/1997 |
| DE | 19827957 A1 | 12/1999 |
| DE | 19840157 C2 | 6/2000 |

OTHER PUBLICATIONS

M. Krause, et al., "Extended gate electrode arrays for extracellular signal recordings", Sensors and Actuators B 70 (2000) 101-107.

W.H. Baumann, et al., "Microelectronic sensor system for microphysiological application on living cells", Sensors and Actuators B 55 (1999) 77-89.

Bjorn Eversmann, et al., "A 128 X 128 CMOS Biosensor Array for Extracellular Recording of Neural Activity", IEEE Journal of Solid-State Circuits, vol. 38, No. 12, Dec. 2003.

Markus Simon Brenner, "Interface zwischen 2000-Transistoren-Chip and neuronaler Zellkulter", Max-Planck-Institut fur Biochemie Abteilung Membran-und Neurophysik, Die Dissertation wurde am 28.11.2000 bei der Technischen Universitat Munchen eingereicht und durch die Fakultat fur Physik am 12.02.101 angenommen.

* cited by examiner

FIELD EFFECT TRANSISTOR FOR MEASURING BIOCOMPONENTS

BACKGROUND OF THE INVENTION

1. Field of the Invention

The invention relates to a device for measuring biological components, especially live cells, that has at least one field effect transistor, which has on a substrate a source, a drain, and a channel area that connects said source and drain. On top of the channel area a gate electrode is arranged, which is electrically insulated from the channel area by a thin insulation layer.

2. Description of Related Art

Such a device is disclosed in DE 196 23 517 C1. It has a field effect transistor in which the gate electrode is electrically connected by a circuit path to an open contact pad surrounded by an electrical insulator. The dimensions of the open contact pad are constructed such that it can contact a live biological cell contained in a nutrient solution. Such a device allows the extracellular measurement of the action potential of a cell that is mounted onto the contact pad, especially a nerve or muscle cell. The substrate of the field effect transistor consists of silicon, in which a tub-like semiconductor layer of a first charge carrier has been set. In this semiconductor layer, endowed drain and source regions are arranged, in between which a channel area is formed. On top of the channel area is a thin insulation layer and on top of it the gate electrode. The gate electrode consists of poly-silicon and covers the complete channel area as well as the neighboring edges of the drain and the source. The gate electrode forms an isoelectric region that distributes an electrical potential bordering it over the complete channel length stretching from the drain to the source, such that the potential reaches also the places where the channel area shows its highest sensitivity even if the field effect transistor is saturated when an asymmetrical, one-sided distribution of free charge carriers in the channel area occurs along the channel length. The disadvantage of the device, however, is that its measurement sensitivity is strongly reduced if the contact pad that is connected to the gate is only partially covered by the cell such that the nutrient solution, which contains the cell, contacts other regions of the contact pad. The decrease in measurement sensitivity occurs mainly because the voltage, which is essentially capacitatively interlinked by the biological cell into the contact pad and thus also the gate electrode, of the initial voltage corresponds to a replacement voltage source with high source resistance. Due to the ions contained in it, the nutrient solution is relatively low-ohmic in comparison to the source resistance. Thus, the measured signal next to the gate is correspondingly reduced when the replacement voltage source is burdened with the electrical resistance of the nutrient solution. The cell signal to be measured is then essentially short-circuited due to the nutrient solution lying over a reference potential, that is, the majority of the voltage does not occur on the gate but rather drops due to the source resistance of the replacement voltage source. It is also unfortunate that the arrangement consisting of the gate electrode, the conducting path, and the contact pad has a relatively large electrical capacitance for the nutrient solution, which in addition weakens the measurement signal.

Therefore, the objective is to design a device as mentioned above, wherein the danger is reduced that the measurement signal results through a contact of the gate electrode with a nutrient solution containing the biological component(s) to be measured.

SUMMARY OF THE INVENTION

This objective is solved in that the gate electrode consists of at least two electrode regions arranged laterally next to each other. These regions are separated perpendicularly to the direction in which the channel area connects the source to the drain, and are electrically insulated from each other.

The gate electrode is advantageously divided into several electrode regions that are electrically insulated from each other, which are perpendicularly offset to a line that connects the source and drain directly to each other and corresponds roughly to the direction of the current flow in the channel area. If a biological component contained in a nutrient solution, upon which component a measurement is being made with the help of the field effect transistor, covers the gate electrode only partially such that at least one electrode region of the gate electrode contacts the nutrient solution directly and at least a second electrode region is covered completely by the biological component and is insulated by this biological component from the nutrient solution, a direct equipotential bonding between the first and the second electrode region, and thus a stress of the voltage lying on the second electrode region with the electrical resistance of the nutrient solution, which is in contact with the first electrode region and is lying on a reference potential, is avoided. Furthermore, the capacitative stress of the measurement signal is reduced through parasitic capacitances due to the divided gate electrode, in contrast to a device with a one-piece gate electrode. Through this, the device advantageously provides a relatively high measurement and detection sensitivity when the biological component covers the gate electrode only partially. In particular, electrical potentials fitted to the individual electrode regions can be interlinked into the partial region of the channel area in which the channel area shows its highest sensitivity when the field effect transistor is used at its saturation level. The device is preferentially designed such that the biological component to be measured can be immobilized directly at the gate electrode. The device allows a high-ohmic signal detection for the biological component.

It would be advantageous if the device had at least three, principally at least five, and preferably at least seven electrode regions in a row. If the biological component covers the gate electrode only partially, an overall higher measuring sensitivity and measuring accuracy for different arrangements of the biological component relative to the gate electrode can therefore be achieved.

In a preferred embodiment of the invention, the edges of the drain and the source bordering the channel area will be approximately parallel to each other, whereby facing electrode edges of neighboring electrode regions run at right angles to the edges of the drain and source bordering the channel area. The borderlines between neighboring electrode regions that are arranged next to each other will then run in about the direction that the flow of the electrical current follows in the channel area. This even more effectively avoids that electrical potentials, which lie against individual electrode regions, influence each other.

In an advantageous embodiment of the invention, an electrical insulating layer is found at both the drain and the source. This layer is preferably an oxide layer with a thickness that is thicker by at least a factor of 10, if needed 30 and preferably 50 than the thickness of the insulating layer, whereby the electrode regions and, where appropriate, the insulating layer
} each laterally border the edge of the insulating layer facing the channel area. This arrangement allows an as of yet small parasitic capacitance between the device surface that is in contact with the nutrient solution during measurement and the source and drain regions, which are separated from this surface.

It is advantageous if the area that is covered by the individual electrode regions at the channel area is smaller or equals the area that is covered by a focal contact of a biological cell that is immobilized on the gate electrode, and if the area that is covered by the individual electrode regions at the channel area principally is between 0.5 and 5 $\mu m^2$. This allows an even higher measuring sensitivity and measuring accuracy for obtaining measurements on live cells that have different sizes and/or are arranged in different positions relative to the gate electrode.

In a functional embodiment of the invention, the insulation layer consists of a silicon-oxide layer, in particular a silicon-dioxide layer, and the gate electrode is a precious metal layer, in particular a palladium layer, whereby a poly-silicon layer is placed between the insulation layer and the gate electrode. This poly-silicon layer is interrupted in the spaces found between neighboring electrode regions. Furthermore, between the poly-silicon layer and the precious metal layer is a precious metal-silicon layer that connects the two. The gate electrode can then be structured through the placement of the interface layer when the device is constructed. For this purpose, first the source and drain regions as well as the channel area are constructed on the endowed semiconductor layer in the field effect transistor (the semiconductor layer can be formed by the substrate or by a tub-like region on top of the substrate), such that subsequently the electrically insulating silicon-oxide layer (gate oxide) can be constructed on the channel area. A poly-silicon layer is placed on top of this layer covering its entire surface, and said layer is then structured such that it remains only at the places where the gate electrode will later be placed. Then, more structured layers are applied to the substrate to form circuit paths. Between individual layers of the circuit path layers, electrical insulating layers are arranged. A passivation layer is applied as a cover layer. Indentations are then etched at the places where the poly-silicon is found. These indentations extend to the poly-silicon layer which serves as an etching stop. If the gate electrode should cover the bottom of the indentations only partially, the poly-silicon layer will be structured in the indentations. Subsequently, metal plating is applied over the entire surface with a precious metal. In a subsequent heat treatment, silicon diffuses from the poly-silicon layer into the precious metal layer and forms a precious metal silicide in a region of the precious metal layer that is a separate from the surface of the precious metal layer. In this way, based on the structure of the poly-silicon layer, the precious metal adheres better to the poly-silicon layer than to the rest of the surface such that it can be mechanically structured, for example with the help of ultrasound waves. By this means, the precious metal dissolves only at the places that are not in contact with the poly-silicon layer.

The device according to the invention is preferably equipped such that the biological component can be directly brought into contact with the gate electrode, which is arranged on the channel area, that is, the biological component is preferably located on the side of the gate electrode opposite of the channel area directly above the channel area during measurement. This arrangement leads to a small parasitic capacitance at the gate electrode. For this purpose, the gate electrode preferably borders a measuring chamber or a trough for the reception of the biological component and, if needed, a nutrient solution containing it.

The invention also covers solutions where individual electrode regions are each connected to an electric contact pad via a circuit path. This pad is located in a port for the biological component that is separate from the gate electrode such that the biological component can be contacted. This arrangement is preferred if a spatial separation between the actual field effect transistor and the biological component(s) is of advantage.

In a functional embodiment of the invention, the device has several field effect transistors, whereby these field effect transistors are preferably arranged in matrix-form next to each other on a common semiconductor substrate. This arrangement makes a location-independent measurement of the signal possible on the biological components.

In an advantageous embodiment of the invention, at least one electrode region of the gate electrode and/or, in addition to the electrode regions and neighboring these, a stimulating electrode is connected to an electrical stimulation device for the biological component. The stimulation device has an electrical voltage source that can be connected with the electrode region and/or the stimulation electrode via an electrical switch. With the help of this device the distribution of electrical signals and/or signal patterns in a cell culture can be examined for cell cultures that have several nerve cell networks. For this purpose, first an electrical stimulation potential is placed on at least one electrode region and/or onto a stimulation electrode, and subsequently removed, such that the response of the cell(s) to the stimulation potential can be measured using the electrode regions.

BRIEF DESCRIPTION OF THE DRAWINGS

Design examples of the invention are explained in more detail below, with reference to the drawings. Shown are.

DETAILED DESCRIPTION OF THE PREFERRED EMBODIMENTS

Figure 1:
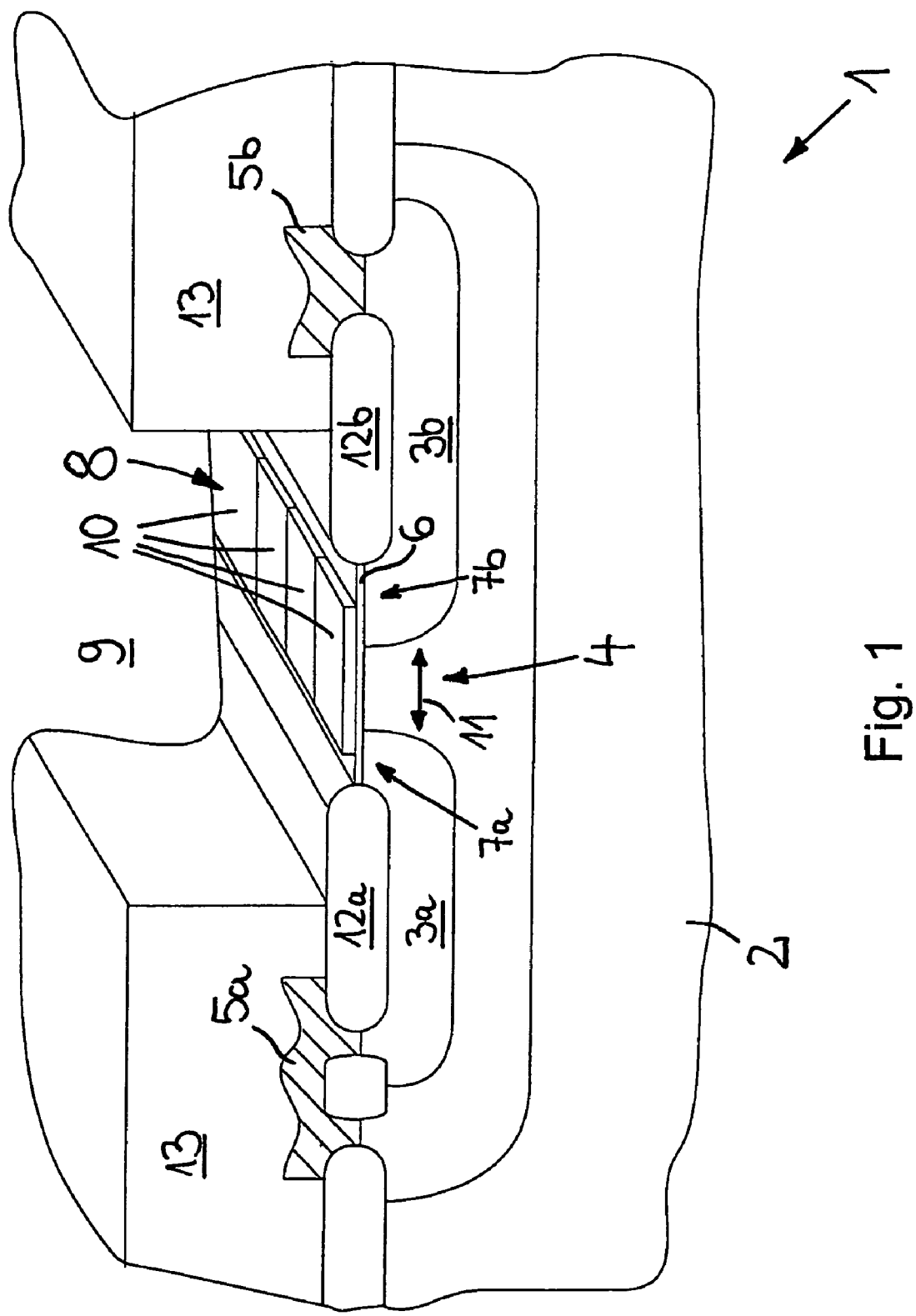
FIG. 1 a three-dimensional partial view of a device with a field effect transistor for conducting measurements on biological components, whereby the device is shown as a cross section in the area of the field effect transistor.

A device designed to measure extracellular cell potentials on live biological cells has a semiconductor chip in which at least one field effect transistor 1 is integrated, which is connected to a measurement amplifier that is not shown in detail in the figure. In the design example shown in FIG. 1, the semiconductor chip has an endowed semiconductor layer 2 of a first charge carrier type. This semiconductor layer is formed by the substrate of the semiconductor chip. However, other design examples are also possible in which the semiconductor layer 2 is embedded into the semiconductor substrate as a tub-form endowed well.

Endowed regions of a second charge carrier type are arranged on the semiconductor layer 2 of which one region forms the source 3a and the other region forms the drain 3b of the transistor 1 when it is connected to the measurement amplifier. It can be seen in FIG. 1 that the source 3a and the drain 3b are embedded in the surface of the semiconductor layer 2 and are laterally separated from each other by a channel area 4 that exists between them. The source 3a is connected to the source contact 5a and the drain 3b is connected to the drain contact 5b at a location removed from the channel area 4. Both contacts are attached to the measurement amplifier. It can be seen at the right side of FIG. 5 that the source contact 5a is also attached to the semiconductor layer 2 (substrate).

An insulation layer 6 is arranged on the channel area 4. This layer consists of a thin oxide layer and extends continuously over the channel area 4 and both adjacent border areas 7a and 7b of the source 3a and the drain 3b. On top of the insulation layer 6 is a structured poly-silicon layer, which is not shown in detail in the figure, in which a gate electrode overall designated with 8 is arranged. This electrode is formed by metal plating. The metal plating consists of a corrosion-resistant precious metal, preferably palladium. In the transition area from the poly-silicon layer to the gate electrode 8, a metal-silicide layer is formed. Thus, the gate electrode 8 is well adhered to or firmly connected with the poly-silicon layer. The gate electrode 8 is directly adjacent to a receiving area 9 that is formed for the reception of live cells found in a nutrient solution 15.

Figure 2:
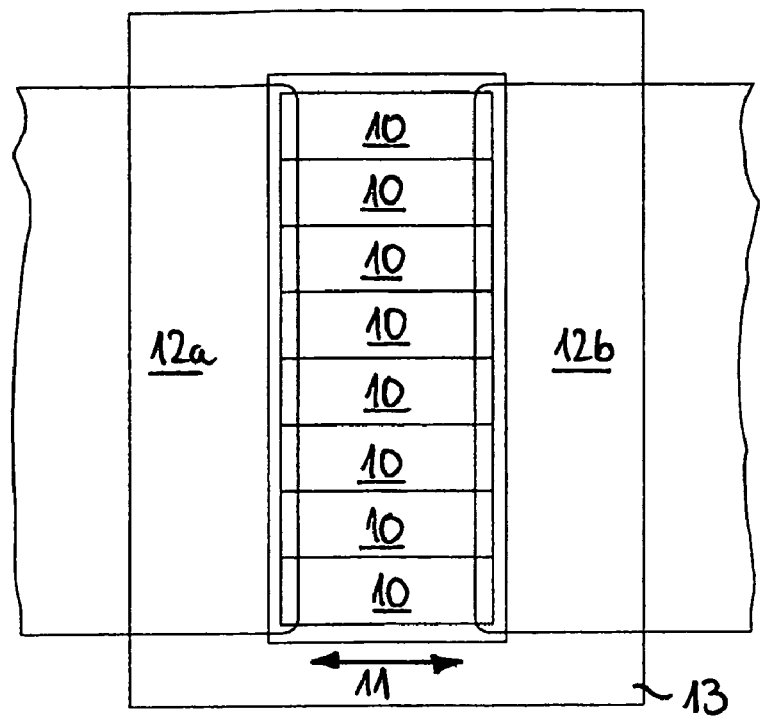
FIG. 2 top view of the device shown in FIG. 1 in the area of the field effect transistor. A structured gate coating can be seen.

As can be seen especially well in FIG. 1, the gate electrode 8 has several laterally adjacent electrode regions 10 that are electrically insulated from each other and are separated from each other parallel to the extension level of the semiconductor chip, approximately at a right angle to the direction marked by the double arrow 11 in FIG. 1 in which the channel area 4 connects the source 3a to the drain 3b. The individual electrode regions 10 are each arranged approximately in the form of a rectangle and extend, uninterrupted across the channel area 4, in the direction 11 in which the channel area 4 connects the source 3a to the drain 3b. It can be seen in FIG. 2 that the electrode regions 10 each cover the source 3a border area 7a, which is adjacent to the channel area 4, with one end and the drain 3b border area 7b, which is adjacent to the channel area 4, with their other end.

Neighboring electrode regions 10 are each separated by a small space, which proceeds approximately at a right angle to the source 3a and drain 3b borders adjacent to the channel area 4. Parallel to these borders, the electrode regions 10 are offset in a direct line to each other such that altogether an oblong gate electrode 8 results that is approximately in the form of a rectangle and consists of several electrode regions arranged in a row. Measurements of a biological cell are adjusted for this electrode. It can be seen in FIG. 2 that the source 3a and the drain 3b each extend without interruption over all electrode regions 10 of the gate electrode 8.

An electrical insulation layer 12a, 12b is arranged on top of the source 3a and the drain 3b at a distance from the channel area 4. This layer consists of a dioxide layer and its thickness is larger than that of the insulation layer 6. The electrode regions 10 and the insulation layer 6 each border laterally with their one end on the insulation layer 12a located on the source 3a and with their other end on the insulation layer 12b located on the drain 3b. On top of the insulation layers 12 a, 12 b is a passivation layer 13 as a top layer, which ends at a distance from the gate electrode such that this electrode is accessible.

Figure 3:
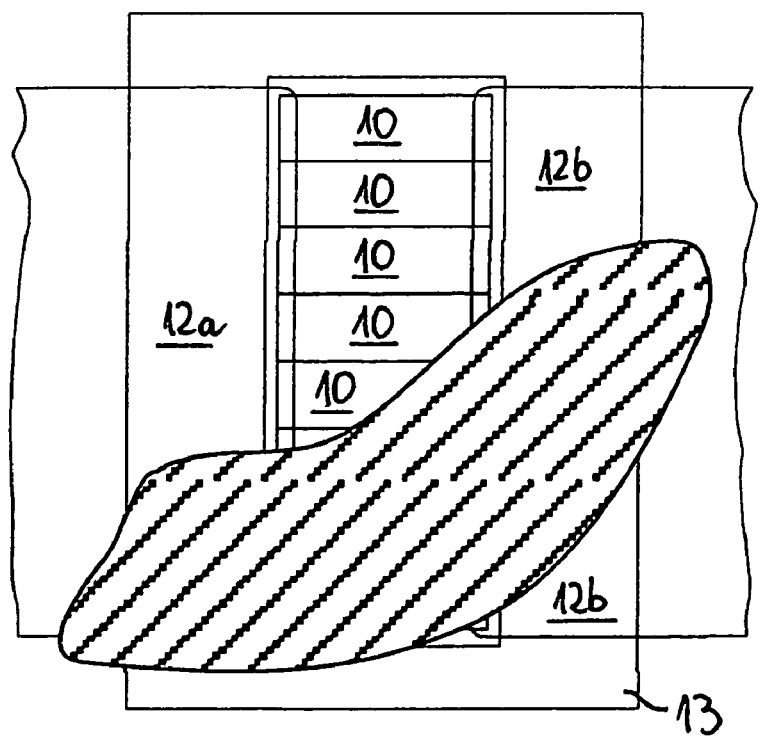
FIG. 3 a partial view of the device in operational mode.

FIG. 3 is a top view of the device in operational mode. It can clearly be seen that a biological cell 14 is immobilized on the surface of the semiconductor chip. This cell is in a nutrient solution 15 (FIG. 4) that is located over a reference electrode on an electrical reference potential not shown in detail in the figure, such as the potential adjacent to source contact 5a. The cell 14 is positioned in relationship to the gate electrode 8 such that some of the electrode regions 10 are completely covered. In this way, the cell adheres to these electrode regions 10 and to the adjacent surface areas of the semiconductor chips, which are electrically insulated against the electrode regions 10, such that the cell 14 isolates the electrode regions 10 against the nutrient solution 15. The remaining electrode regions 10 are at least partially in contact with the nutrient solution 15 and thus lie on the reference potential adjacent to the nutrient solution 15. Because the gate electrode 8 is divided into several electrode regions 10, it is avoided that the cell potential, which is connected from the cell via the cell membrane to the electrode region 10 that are isolated by the cell 14 against the nutrient solution 15, is pulled onto the relatively low-ohmic reference potential. The device thus allows a precise measurement of the changes in cell potential even if the gate electrode 8 is only partially covered by the cell 14.

Figure 4:
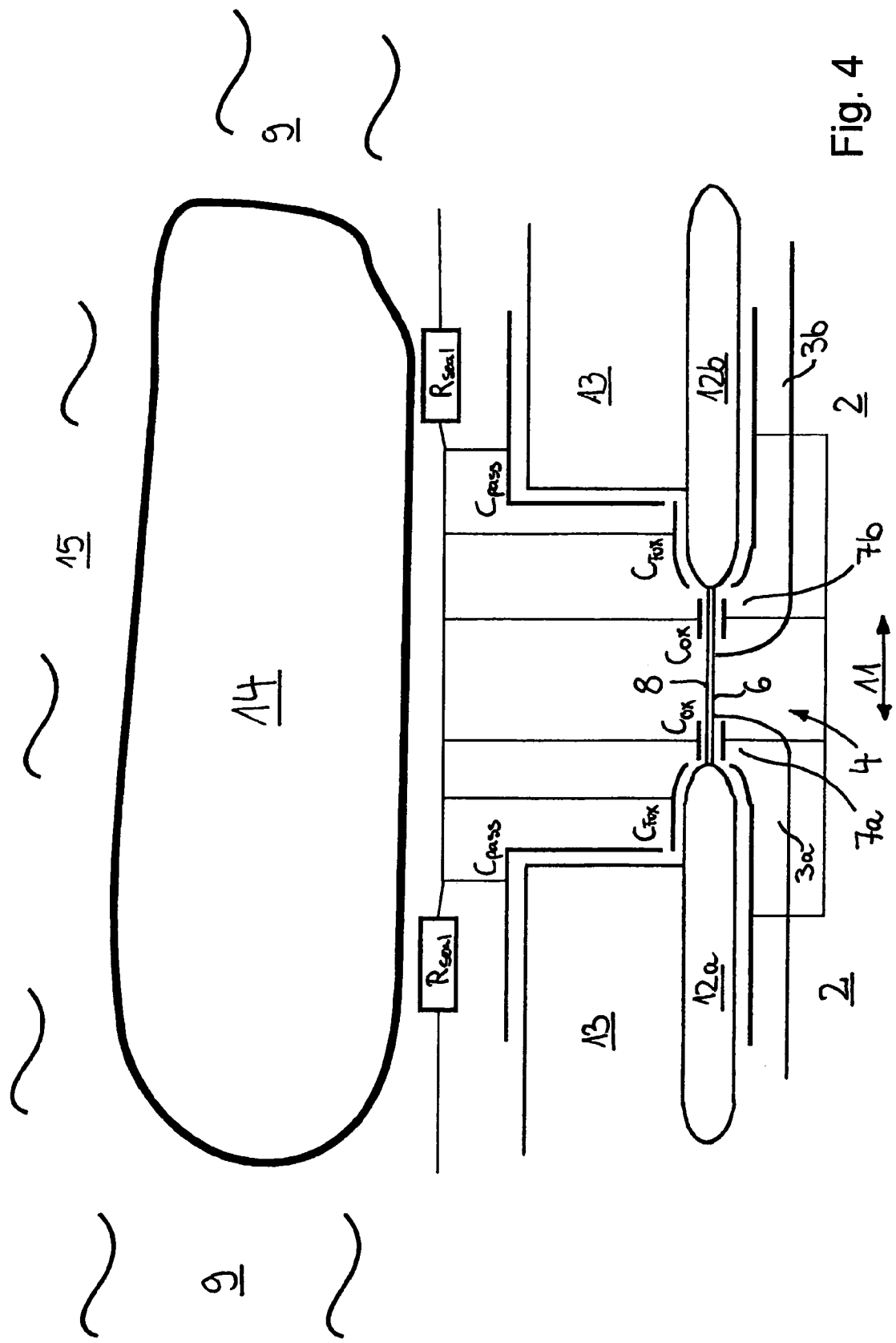
FIG. 4 a cross section of the device schematically illustrating parasitic capacitances.

FIG. 4 is a schematic illustration of an electrical equivalent circuit diagram showing the electrical capacitances, which are formed by the device in the region covered by the cell 14. It can clearly be seen that the condenser plates of the equivalent condenser $C_{Fox}$ for the electrical capacitances formed by the insulation layers 12 a, 12b and the condenser plates of the equivalent condenser $C_{Pass}$ for the electrical capacitances formed by region of the passivation layer 13 covered by the cell 14 are each much further separated from each other than the condenser plates of the equivalent condenser $C_{ox}$ for the electrical capacitances formed by the gate electrode 8. Thus, the capacitances $C_{Fox}$ and $C_{Pass}$ are much smaller than the overall capacitance of the gate electrode 8. Because this capacitance is divided into several electrode regions that are electrically insulated from each other on the semiconductor chip, the capacitive charge that affects the measurement signal through the capacitance $C_{ox}$ is also relatively small. Thus, the device allows altogether a high measurement sensitivity and a broad-spectrum measurement signal, which is essentially undistorted.

In FIG. 4 an ohmic equivalent resistance $R_{seal}$ can also be seen, which reproduces the seal resistance over which the area of the cell membrane, which is arranged within the contact area of the cell and removed from the edge of the contact area, is connected with the electrical capacitance that is formed between the area of the passivation layer 13, which is outside the contact area of the cell, and the semiconductor layer 2. The cell 14 isolates the surface of the passivation layer 13 when it is in contact with it. In FIG. 4, the distance between the cell membrane and the passivation layer 13 has been greatly enlarged for reasons of better clarity.

The invention claimed is:

1. A device for conducting measurements on biological components in a nutrient solution, especially on live cells, containing at least one field effect transistor that has on a substrate a source, a drain, and a channel area connecting said source and drain on which a gate electrode that is insulated from the channel area by a thin insulation layer is arranged, whereby the gate electrode has at least two electrode regions arranged laterally next to each other, which are separated from each other perpendicular to the direction in which the channel area connects the source electrode to the drain and are electrically insulated from each other, and whereby the electrode regions have at least partial contact to the nutrient solution that lies on an electric reference potential over a reference electrode.

2. The device as defined in claim 1, characterized in that at least three, principally at least five, and preferably at least seven of the electrode regions are arranged in a row next to each other.

3. The device as defined in claim 1, characterized in that the edges of the drain and the source bordering the channel area run approximately parallel to each other and that facing electrode edges of neighboring electrode regions each run at approximately right angles to the edges of the drain and/or the source bordering the channel area, respectively.

4. The device as defined in claim 1, characterized in that an electrical insulation layer is arranged on the drain and the source, respectively, which is preferably an oxide layer whose thickness is thicker by a factor of at least 10, if applicable 30, and preferably 50 than the insulation layer, and that the electrode region and, if applicable, the insulation layer border laterally directly on the edges of the insulation layer facing the channel area.

5. The device as defined in claim 1, characterized in that the area that is covered by the individual electrode regions at each channel area respectively, is smaller or equal to the area that covers a focal contact of a biological cell that can be immobilized on the gate electrode, and is preferably between 0.5 and 5 $\mu m^2$.

6. The device as defined in claim 1, characterized in that the insulation layer is designed as a silicon-oxide layer, in particular as a silicon-dioxide layer, and the gate electrode as a precious metal layer, in particular as a palladium layer, that between the insulation layer and the gate electrode a poly-silicon layer is arranged, which is interrupted in the spaces between the neighboring electrode regions, and that there is a precious metal silicide layer between the poly-silicon layer and the precious metal layer, which connects the two.

7. The device as defined in claim 1, characterized in that the gate electrode borders directly onto a measurement chamber or a trough for the reception of the biological component(s) and, if necessary, a nutrient solution containing said biological component(s).

8. The device as defined in claim 1, characterized in that the individual electrode regions are each connected by a circuit path with the electrical contact elements, which—for contact with the biological component—is arranged in a biological component contact area separate from the gate electrode.

9. The device as defined in claim 1, characterized in that it has several field effect transistors, and that these field effect transistors are preferably arranged in a matrix-form on top of a common semiconductor substrate.

10. The device as defined in claim 1, characterized in that at least one electrode region gate electrode and/or one existing and neighboring stimulating electrode in addition to the electrode regions is connected to electric stimulation equipment for the biological component.

11. Use of a device designed to measure a signal on a biological cell extracellularly, whereby the device has at least one field effect transistor, which has on a substrate a source, a drain, and a channel area connecting the said source and drain on which a gate electrode is arranged that is electrically insulated from the channel area by a thin insulation layer, whereby the gate electrode has at least two electrode regions arranged laterally next to each other, which are separated from each other perpendicular to the direction in which the channel area connects the source to the drain and are electrically insulated from each other.

* * * * *